United States Patent
Lai et al.

(10) Patent No.: US 8,202,506 B2
(45) Date of Patent: Jun. 19, 2012

(54) HIGH ACTIVITY SMALL CRYSTAL ZSM-12

(75) Inventors: Frank Lai, Bridgewater, NJ (US);
Richard B. Saunders, Wayne, NJ (US);
Kathy Saunders, legal representative, Wayne, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 207 days.

(21) Appl. No.: 12/590,952

(22) Filed: Nov. 17, 2009

(65) Prior Publication Data
US 2011/0118520 A1    May 19, 2011

(51) Int. Cl.
*C01B 39/04* (2006.01)
(52) U.S. Cl. .. 423/708; 423/705; 423/716; 423/DIG. 33
(58) Field of Classification Search .................. 423/705, 423/716, DIG. 33, 708
See application file for complete search history.

(56) References Cited

U.S. PATENT DOCUMENTS

| | | | |
|---|---|---|---|
| 4,585,639 A | | 4/1986 | Szostak |
| 6,893,624 B2 * | | 5/2005 | Lai et al. ........................ 423/705 |
| 2004/0097363 A1 * | | 5/2004 | Johnson et al. .................. 502/64 |
| 2008/0035525 A1 * | | 2/2008 | Burgfels et al. ................. 208/26 |

FOREIGN PATENT DOCUMENTS
WO    2004046034    6/2004

OTHER PUBLICATIONS

R. Aiello, G. Giordano, F. Testa; "Impact of zeolites and othe porous materials on the new technologies at the beginning of the new millennium," Studies in Surface Science and Catalysis, vol. 142, Proceedings of the 2nd International FEZA Conference, Taormina, Italy, Sep. 1-5, 2002, pp. 247-254.
Jiri Cejka, Gabriela Kosova, Nadezda Zilkova, Irena Hruba, "(A1)-ZSM-12: Synthesis and modification of acid sites", Studies in Surface Science and Catalysis vol. 142A, (Jan. 1, 2002), pp. 247-254, XP008028026.

* cited by examiner

*Primary Examiner* — David M Brunsman
(74) *Attorney, Agent, or Firm* — Liza Montalvo; David Weisberg

(57) ABSTRACT

A porous, crystalline material is described having the framework structure of ZSM-12 and a composition involving the molar relationship:

$$X_2O_3:(n)YO_2$$

wherein X is a trivalent element, Y is a tetravalent element and n is less than about 45, e.g., less than about 40, wherein the average crystal size of the material is less than about 0.1 micron, which material is substantially free of impurities. The material is made by: (a) preparing a mixture capable of forming said material, said mixture comprising sources of alkali or alkaline earth metal (M), an oxide of trivalent element (X), an oxide of tetravalent element (Y), hydroxyl ($OH^-$) ions, water, and an organic monoquaternary ammonium cation directing agent (R) and an organic diquaternary ammonium structure blocking agent (R'); (b) maintaining the mixture under sufficient conditions until crystals of said material are formed; and (c) recovering the crystalline material from step (ii). The material can be used as a hydrocarbon conversion process catalyst.

17 Claims, 3 Drawing Sheets

XRD of Example 1

HIGH ACTIVITY SMALL CRYSTAL ZSM-12

FIELD

This invention relates to highly purified, high activity, small crystal ZSM-12, its synthesis and its use in catalytic processes, particularly in the conversion of $C_9+$ aromatic hydrocarbons to xylenes.

BACKGROUND

ZSM-12 and its conventional preparation in the presence of a tetramethylammonium or tetraethylammonium directing agent are taught by U.S. Pat. No. 3,832,449, the entire disclosure of which is incorporated herein by reference. ZSM-12 has a distinctive X-ray diffraction pattern which distinguishes it from other known crystalline materials.

There is a growing demand for ZSM-12-type catalyst materials in the chemical and refining fields. As a result there is significant interest in developing improved techniques for the synthesis of ZSM-12.

U.S. Pat. No. 4,391,785 discloses a method for the synthesis of ZSM-12 from a reaction mixture comprising, as a directing agent, a compound selected from the group consisting of a dimethylpyridinium halide and a dimethylpyrrolidinium halide.

U.S. Pat. Nos. 4,452,769 and 4,537,758 disclose methods for synthesizing ZSM-12 from a reaction mixture containing methyltriethylammonium ions as the directing agent. These patents are primarily directed to producing high $SiO_2/Al_2O_3$ ratio forms of ZSM-12, greater than 80 in the case of the '769 patent and greater than 200 in the case of the '758 patent. Moreover, one of the stated advantages in the '769 patent of using methyltriethylammonium ions as the directing agent is the production of large crystal size materials.

Other organic directing agents that have been used to synthesize ZSM-12 include DABCO-$C_n$-diquat ions where n=4, 5, 6 or 10 (see U.S. Pat. No. 4,482,531), bis(dimethylpiperidinium)trimethylene ions (see U.S. Pat. No. 4,539,193), benzyltriethylammonium ions (see U.S. Pat. No. 4,552,738), dibenzyldiethylammonium ions (see EP-A-167,232), dimethyldiethylammonium ions (see U.S. Pat. No. 4,552,739), benzyltrimethylammonium ions (see U.S. Pat. No. 4,585,637), bis(N-methylpyridyl)ethylinium ions (see U.S. Pat. No. 4,585,746), hexamethyleneimine (U.S. Pat. No. 5,021,141), and decamethonium ions (see U.S. Pat. No. 5,192,521) bis(methylpyrrolidinium) diquat-n ions where n=4, 5, or 6.

Although influenced by variables such as the silica/alumina molar ratio of the reaction mixture, temperature and stirring, the crystal morphology of synthetic zeolites, such as ZSM-12, is mainly dominated by the choice of directing agent used in the crystallization. For example, in the case of ZSM-12, needle-shaped crystals can be produced using a benzyltrimethylammonium directing agent, rice-shaped crystals can be made in the presence of tetraethylammonium salts, and bundles of hexagonal platelets can be prepared from a hexamethyleneimine directing agent. The control of zeolite crystal morphology is very important from the standpoint of activity and stability enhancement. For most catalytic applications, small crystal size is desirable for high activity and stability because of the higher surface area, and hence the shorter diffusion path, of small crystal materials.

For example, U.S. Pat. No. 6,893,624 discloses the synthesis of ZSM-12 having a silica to alumina molar ratio less than 60, an average crystal size of the material is less than 0.1 micron and a Diffusion Parameter for mesitylene of at least $1000 \times 10^{-6}$ sec$^{-1}$ when measured at a temperature of 100° C. and a mesitylene pressure of 2 torr. The synthesis is conducted by crystallizing a reaction mixture comprising a source of an oxide of a trivalent element X, a source of an oxide of a tetravalent element Y, methyltriethylammonium cations (R) as a template, an alkali metal and/or alkaline earth metal ion source M having the valency n and water; wherein the mixture has the following composition in terms of the molar ratios: $YO_2/X_2O_3$ is 40 to 80, $H_2O/YO_2$ is 15 to 40, $OH^-/YO_2$ is 0.15 to 0.4, $M/YO_2$ is 0.15 to 0.4 and $R/YO_2$ is 0.15 to 0.4. The crystallization is carried out at a temperature of 170° C. or less for a time of about 50 to 500 hr.

In addition, US Patent Application Publication No. 2008/0035525 discloses a process for producing ZSM-12 having a primary crystal size of <0.1 µm; and a specific volume, determined by mercury porosimetry at a maximum pressure of 4000 bar, of 30-200 mm$^3$/g in a pore radius range of 4-10 nm. The process involves crystallization of a synthesis gel composition comprising an aluminum source, precipitated silica as a silicon source, TEA$^+$ as a template, an alkali metal and/or alkaline earth metal ion source M having the valency n and water; in which the molar $H_2O:SiO_2$ ratio is selected between 5 and 15, the molar $M_{2/n}O:SiO_2$ ratio is within the range from 0.01 to 0.045, molar TEA$^+$/SiO$_2$ ratio is between about 0.10 and 0.18, the molar $SiO_2/Al_2O_3$ ratio is within a range from 50 to 150. The crystallization is carried out at a temperature of from about 120 to 200° C., preferably from about 140 to 180° C., for a time of about 50 to 500 hr, in particular from about 100 to 250 hr.

An object of the present invention is to provide a small crystal, high activity form of ZSM-12 which exhibits enhanced activity in the conversion of $C_9+$ aromatic hydrocarbons to xylenes.

It is to be appreciated that, although ZSM-12 is normally synthesized as an aluminosilicate, the framework aluminum can be partially or completely replaced by other trivalent elements, such as boron and/or iron and/or gallium, and the framework silicon can be partially or completely replaced by other tetravalent elements such as germanium.

SUMMARY

In one aspect, the invention resides in a porous, crystalline material having the framework structure of ZSM-12 and a composition involving the molar relationship:

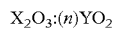

wherein X is a trivalent element, Y is a tetravalent element and n is less than about 45, wherein the average crystal size of the material is less than about 0.1 micron, which material is substantially free of ZSM-5 or mordenite impurities. By "substantially free of ZSM-5 impurities" is meant that the composition contains no ZSM-5 phase as measured by X-Ray Diffraction.

Preferably, the material has a value of n which is about 20 to less than about 40, e.g., n is about 30 to about 36.

Preferably, X is aluminum and Y is silicon.

Preferably, the material has an alpha value in excess of 500, e.g., in excess of 550.

Preferably, the material has a Diffusion Parameter for mesitylene of at least $1000 \times 10^{-6}$ sec$^{-1}$ when measured at a temperature of 100° C. and a mesitylene pressure of 2 torr.

In another aspect, the present invention relates to a porous, crystalline material having the framework structure of ZSM-12 and a composition in terms of mole ratios of oxides as follows:

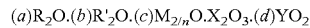

wherein R is an organic monoquaternary ammonium cation, R' is at least one organic diquaternary ammonium, M is at least one cation having a valence n, X is a trivalent element, Y is a tetravalent element, a ranges from about 0.01 to about 2, b ranges from about 0 to about 0.5, c ranges from about 0.01 to about 2, and d ranges from about 20 to about 100.

Preferably, M is sodium, X is aluminum, and Y is silicon.

Preferably, R is $R^1R^2R^3R^4N^+$ wherein each of $R^1$, $R^2$, $R^3$, and $R^4$ are the same or different and selected from the group consisting of $C_1$ to $C_4$ alkyls, R' is $R^5R^6R^7N^+(CH_2)_mN^+R^8R^9R^{10}$ wherein each of $R^5$, $R^6$, $R^7$, $R^8$, $R^9$, and $R^{10}$ are the same or different and selected from the group consisting of $C_1$ to $C_4$ alkyls.

Preferably, R is methyltriethylammonium and R' is polymethylene bis-trimethylammonium.

Preferably, R' is hexamethonium.

In another aspect, the present invention relates to a process for synthesizing the porous, crystalline material of porous, crystalline material having the framework structure of ZSM-12 and a composition involving the molar relationship:

$$X_2O_3:(n)YO_2$$

wherein X is a trivalent element, Y is a tetravalent element and n is less than about 45, wherein the average crystal size of the material is less than about 0.1 micron, which material is substantially free of impurities. The process comprises: (a) preparing a mixture capable of forming said material, said mixture comprising sources of alkali or alkaline earth metal (M), an oxide of trivalent element (X), an oxide of tetravalent element (Y), hydroxyl ($OH^-$) ions, water, and an organic monoquaternary ammonium cation directing agent (R) and an organic diquaternary ammonium structure blocking agent (R'), wherein said mixture has a composition, in terms of mole ratios, within the following ranges:

$YO_2/X_2O_3$=less than 50
$H_2O/YO_2$=10 to 100
$OH^-/YO_2$=0.1 to 0.6
$M/YO_2$=0.1 to 0.6
$R/YO_2$=0.1 to 0.6
$R'/R$=0.01 to 0.10

(b) maintaining said mixture under sufficient conditions until crystals of said material are formed; and (c) recovering said crystalline material from step (ii).

Preferably, R=$R^1R^2R^3R^4N^1$ wherein each of $R^1$, $R^2$, $R^3$, and $R^4$ are the same or different and selected from the group consisting of $C_1$ to $C_4$ alkyls, R' is $R^5R^6R^7N^+(CH_2)_mN^+R^8R^9R^{10}$ wherein each of $R^5$, $R^6$, $R^7$, $R^8$, $R^9$, and $R^{10}$ are the same or different and selected from the group consisting of $C_1$ to $C_4$ alkyls, and said reaction mixture has a composition in terms of mole ratios within the following ranges:

$YO_2/X_2O_3$=30 to 40
$H_2O/YO_2$=15 to 40
$OH^-/YO_2$=0.15 to 0.4
$M/YO_2$=0.15 to 0.4
$R/YO_2$=0.15 to 0.4
$R'/R$=0.02 to 0.03

Preferably, R is methyltriethylammonium and R' is polymethylene bis-trimethylammonium.

Preferably, R' is hexamethonium.

Preferably, the conditions include a temperature of 170° C. or less.

Preferably, the conditions include a temperature of 140° C. to 160° C.

In still another aspect, the present invention relates to a process for converting $C_9$+ alkylaromatic hydrocarbons to a product including xylenes, comprising the step of contacting a feed containing $C_9$+ alkylaromatic hydrocarbons together with toluene and/or benzene under conversion conditions with the porous crystalline materials described above.

Preferably, n is 20 to less than 40, X is aluminum and Y is silicon, the porous, crystalline material has an alpha value in excess of 500, and the conversion conditions include a temperature of from about 650 to about 950° F. (340 to 510° C.), a pressure of from about 100 to about 600 psig (790 to 4240 kPa), a weight hourly space velocity of between about 0.1 and about 200 $hr^{-1}$, and a hydrogen to hydrocarbon molar ratio of between about 1 and about 5.

Preferably, the feed is also contacted with a second molecular sieve having a constraint index of 3 to 12.

DETAILED DESCRIPTION

Figure 1:
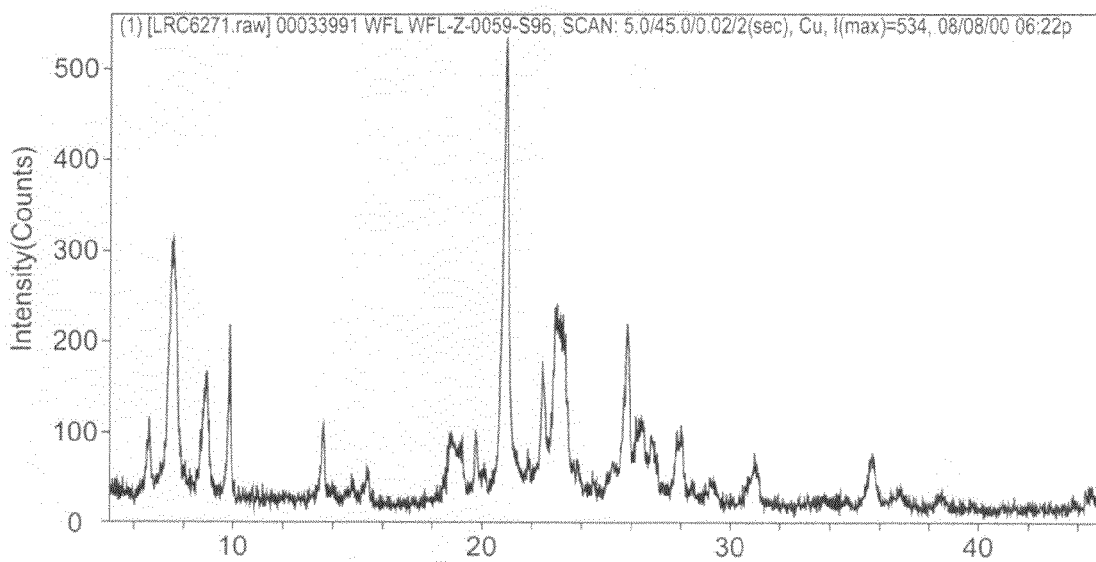
FIG. 1 is XRD of the as-synthesized material of Example 1.

The ZSM-12 according to the invention has an X-ray diffraction pattern characterized by the X-ray diffraction lines in Table 1 below:

TABLE 1

| D-spacing (Å) | Relative Intensity [100 × I/Io] |
|---|---|
| 11.9 ± 0.2 | m |
| 10.1 ± 0.2 | m |
| 4.76 ± 0.1 | w |
| 4.29 ± 0.08 | vs |
| 3.98 ± 0.08 | m |
| 3.87 ± 0.07 | vs |
| 3.49 ± 0.07 | w |
| 3.38 ± 0.07 | m |
| 3.20 ± 0.06 | w |
| 3.05 ± 0.05 | w |
| 2.54 ± 0.03 | w |

The X-ray diffraction data was collected with a Scintag diffractometer using copper K-alpha radiation. The diffraction data were recorded by step-scanning at 0.02 degrees of two-theta, where theta is the Bragg angle, and a counting time of 1 second for each step. The interplanar spacings, d's, were calculated in Angstrom units (A), and the relative intensities of the lines, I/Io, where Io is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (75-100), s=strong (50-74), m=medium (25-49) and w=weak (0-24). It should be understood that diffraction data listed for this sample as single lines may consist of multiple overlapping lines which under certain conditions, such as differences in crystallite sizes or very high experimental resolution or crystallographic change, may appear as resolved or partially resolved lines. Typically, crystallographic changes can include minor changes in unit cell parameters and/or a change in crystal symmetry, without a change in topology of the structure. These minor effects, including changes in relative intensities, can also occur as a result of differences in cation content, framework composition, nature and degree of pore filling, and thermal and/or hydrothermal history.

The crystalline material ZSM-12 of the present invention has a composition involving the molar relationship:

$$X_2O_3:(n)YO_2$$

wherein X is a trivalent element, such as aluminum, boron, iron, indium and/or gallium, preferably aluminum; Y is a tetravalent element, such as silicon, tin and/or germanium, preferably silicon; and n is less than about 45, say, less than about 40, preferably is about 20 to less than about 40, more preferably about 30 to about 36.

In its as-synthesized form, the crystalline material of the invention has the framework structure of ZSM-12 and a composition in terms of mole ratios of oxides as follows:

$$(a)R_2O.(b)R'_2O.(c)M_{2/n}O.X_2O_3.(d)YO_2$$

wherein R is organic monoquaternary ammonium cation, R' is an organic diquaternary ammonium, M is at least one cation having a valence n, X is a trivalent element, Y is a tetravalent element, a ranges from about 0.01 to about 2, b ranges from about 0 to about 0.5, c ranges from about 0.01 to about 2, and d ranges from about 20 to about 100. The M, R and R' components are associated with the material as a result of their presence during crystallization and are easily removed by post-crystallization methods hereinafter more particularly described.

The ZSM-12 of the present invention has an average crystal size of the material less than 0.1 micron, and preferably about 0.05 micron, and has a Diffusion Parameter, $D/r^2$, for mesitylene of at least $1000 \times 10^{-6}$ sec$^{-1}$, and preferably at least $2000 \times 10^{-6}$ sec$^{-1}$, when measured at a temperature of 100° C. and a mesitylene pressure of 2 torr.

As used herein, the Diffusion Parameter of a particular porous crystalline material is defined as $D/r^2 \times 10^6$, wherein D is the diffusion coefficient (cm$^2$/sec) and r is the crystal radius (cm). The required diffusion parameters can be derived from sorption measurements provided the assumption is made that the plane sheet model describes the diffusion process. Thus for a given sorbate loading Q, the value $Q/Q_\infty$, where $Q_\infty$ is the equilibrium sorbate loading, is mathematically related to $(Dt/r^2)^{1/2}$ where t is the time (sec) required to reach the sorbate loading Q. Graphical solutions for the plane sheet model are given by J. Crank in "The Mathematics of Diffusion", Oxford University Press, Ely House, London, 1967.

The ZSM-12 of the present invention preferably has an alpha value of at least 400, and more preferably in excess of at least 500, or even in excess of at least 600. The alpha value test is a measure of the cracking activity of a catalyst and is described in U.S. Pat. No. 3,354,078 and in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

Attempts to grow pure phase ZSM-12 crystals with SiO$_2$/Al$_2$O$_3$ below 45, say, below 40, have been problematic, typically resulting in the formation of undesired impurities. The typical impurities found in the synthesized products include the competitive phases of ZSM-5 and/or mordenite which can be identified in X-ray diffraction patterns. The present invention is based on the discovery that the preparation of ZSM-12 from a synthesis mixture containing two types of directing agents, R and R', allows the preparation of small crystal size high activity ZSM-12 free of impurities. Without wishing to be bound by any theory, it appears that the presence of a diquaternary ammonium agent in the synthesis mixture prevents the formation of undesired impurities in the ZSM-12 product, providing highly pure high activity ZSM-12 crystals.

Conveniently, the diquaternary ammonium agent is added to the crystallization mixture in amounts ranging from about 0 to about 5 wt %, preferably from about 0.1 to about 1 wt % of the starting gel mixture. R' is typically defined as $R^5R^6R^7N^+(CH_2)_mN^+R^8R^9R^{10}$ wherein each of $R^5$, $R^6$, $R^7$, $R^8$, $R^9$, and $R^{10}$ are the same or different and selected from the group consisting of $C_1$ to $C_4$ alkyls. Hexamethonium [N,N,N,N',N',N'-hexamethyl-1,6-Hexanediaminium] dication is preferred, with hexamethonium dichloride, being especially preferred.

The materials prepared in accordance with the present invention are substantially free of impurities, such as ZSM-5 or mordenite. The presence of these impurities can be determined and quantified by analysis of the X-ray diffraction pattern of a sample.

The ZSM-12 of the present invention can be produced from a synthesis mixture containing sources of alkali or alkaline earth metal (M) cations, normally sodium; an oxide of a trivalent element (X), normally alumina; an oxide of a tetravalent element (Y), normally silica; tetraalkylammonium ions (R), e.g., methyltriethylammonium ions (R), normally present as the iodide salt; a structure blocking agent (R') which typically comprises at least one organic diquat, e.g., hexamethonium, normally present as a chloride salt, hydroxyl ions and water. The synthesis mixture has a composition, expressed in terms of mole ratios of oxides, as follows:

| Component | Useful | Preferred |
|---|---|---|
| YO$_2$/X$_2$O$_3$ | 20-100 | 30-60 |
| H$_2$O/YO$_2$ | 10-100 | 15-40 |
| OH$^-$/YO$_2$ | 0.1-0.4 | 0.15-0.3 |
| R/YO$_2$ | 0.1-0.6 | 0.15-0.4 |
| R'/YO$_2$ | 0-0.05 | 0.001-0.02 |
| R'/R | 0-0.5 | 0.005-0.05 |
| M/YO$_2$ | 0.1-0.4 | 0.15-0.3 |

The synthesis method of the invention functions with or without added nucleating seeds. In a preferred embodiment, the reaction mixture contains 0.05-5 wt % nucleating seeds of ZSM-12.

Crystallization is carried out under either stirred or static conditions, preferably stirred conditions, at a relatively low temperature of 170° C. or less and preferably 140 to 160° C. Preferably, crystallization is conducted for 48 to 500 hours, after which the resultant ZSM-12 crystals are separated from the mother liquor and recovered.

In its as-synthesized form, the ZSM-12 of the invention contains the organic material(s) used as the directing agent and, prior to use as a catalyst adsorbent, the as-synthesized material is normally treated to remove part or all of the organic constituent. This is conveniently effected by heating the as-synthesized material at a temperature of from about 250° C. to about 550° C. for from 1 hour to about 48 hours.

To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIIB, VIIB and VIII of the Periodic Table of the Elements.

The crystalline material of this invention, when employed either as an adsorbent or as a catalyst in an organic compound conversion process should be dehydrated, at least partially. This can be done by heating to a temperature in the range of 200° C. to about 370° C. in an atmosphere such as air or nitrogen, and at atmospheric, subatmospheric or superatmospheric pressures for between 30 minutes and 48 hours. Dehydration can also be performed at room temperature merely by placing the ZSM-12 in a vacuum, but a longer time is required to obtain a sufficient amount of dehydration.

Synthetic ZSM-12 crystals prepared in accordance herewith can be used either in the as-synthesized form, the hydrogen form or another univalent or multivalent cationic form. It can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such components can be exchanged into the composition, impregnated therein or physically intimately admixed therewith. Such components can be impregnated in or on to the ZSM-12 such as, for example, by, in the case of platinum, treating the material with a platinum metal-containing ion. Suitable platinum compounds for this purpose include chloroplatinic acid, platinous chloride and various compounds containing the platinum amine complex. Combinations of metals and methods for their introduction can also be used.

When used as a catalyst, it may be desirable to incorporate the ZSM-12 of the invention with another material resistant to the temperatures and other conditions employed in certain organic conversion processes. Such matrix materials include active and inactive materials and synthetic or naturally occurring zeolites as well as inorganic materials such as clays, silica and/or metal oxides, e.g. alumina, titania and/or zirconia. The latter may be either naturally occurring or in the form of gelatinous precipitates, sols or gels including mixtures of silica and metal oxides. Use of a material in conjunction with the ZSM-12, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline catalytic materials have been incorporated into naturally occurring clays, e.g. bentonite and kaolin. These materials, i.e. clays, oxides, etc., function, in part, as binders for the catalyst. It is desirable to provide a catalyst having good crush strength because in a petroleum refinery the catalyst is often subjected to rough handling, which tends to break the catalyst down into powder-like materials which cause problems in processing.

Naturally occurring clays which can be composited with the hereby synthesized crystalline material include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the present crystals can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of finely divided crystalline material and matrix vary widely with the crystalline material content ranging from about 1 to about 90 percent by weight, and more usually in the range of about 2 to about 50 percent by weight of the composite.

Aluminosilicate ZSM-12 according to the invention is useful as a catalyst in organic compound, and in particular hydrocarbon, conversion reactions where high activity is important. In particular, when combined with a hydrogenation component, such as platinum, palladium or rhenium, the ZSM-12 is useful in the catalytic conversion of $C_9+$ alkylaromatic hydrocarbons, either alone or in the presence of toluene and/or benzene, to produce xylenes. Such conversion is typically effected at a temperature of from about 650 to about 950° F. (340 to 510° C.), and preferably from about 750 to about 850° F. (400 to 450° C.), a pressure of from about 100 to about 600 psig (790 to 4240 kPa), and preferably from about 200 to about 500 psig (1480 to 3550 kPa), a weight hourly space velocity (WHSV) of between about 0.1 and about 200 $hr^{-1}$, and preferably between about 0.5 and about 20 $hr^{-1}$, and a hydrogen, $H_2$, to hydrocarbon, HC, molar ratio of between about 1 and about 5, and preferably from about 1 to about 3.

Where the ZSM-12 of the invention is used in the catalytic conversion of $C_9+$ alkylaromatic hydrocarbons, the ZSM-12 may be used in combination with a second molecular sieve having a constraint index of 3 to 12, such as ZSM-5, ZSM-11, ZSM-22, ZSM-23, ZSM-35, ZSM-48, ZSM-57 and ZSM-58. The ZSM-12 and second molecular sieve may be arranged in separate is catalyst beds, with the feed cascading from the catalyst bed containing the ZSM-12 to the bed containing the second molecular sieve. Alternatively, the ZSM-12 and second molecular sieve can be combined in a single catalyst bed.

In order to more fully illustrate the nature of the invention and the manner of practicing same, the following examples are presented.

EXAMPLE 1

Comparative

A mixture was prepared from 1028.5 g of water, 90.5 g of methyltriethylammonium chloride (MTEACl), 33.5 g of NaOH (50% aqueous solution), 28.7 g of sodium aluminate (45% aqueous solution), and 195.7 g of Ultrasil silica. The mixture had the following molar composition:

$SiO_2/Al_2O_3$~40
$H_2O/SiO_2$~20
$OH^-/SiO_2$~0.2
$Na^+/SiO_2$~0.2
$MTEACl/SiO_2$~0.19

The mixture was reacted at 335° F. (168° C.) in a 7.6 liter (two gallon) autoclave with stirring at 150 RPM for 96 hours. The product was filtered, washed with deionized (DI) water and dried at 250° F. (120° C.). The XRD pattern of the as-synthesized material, as demonstrated in FIG. 1, showed the resulting product was a mixture of ZSM-12 and mordenite impurity.

EXAMPLE 2

A mixture was prepared from 10,410 g of water, 1,126 g of methyltriethylammonium chloride (MTEACl), 87.5 g of hexamethonium chloride (56% aqueous solution), 325 g of NaOH 50% solution, 265 g of sodium aluminate (45%) solution, and 1,814 g of Ultrasil silica. The mixture had the following molar composition:

$SiO_2/Al_2O_3$~40
$H_2O/SiO_2$~22
$OH^-/SiO_2$~0.2
$Na^+/SiO_2$~0.2
$MTEACl/SiO_2$~0.26
HMDCl/MTEACl~0.026

Figure 2A:
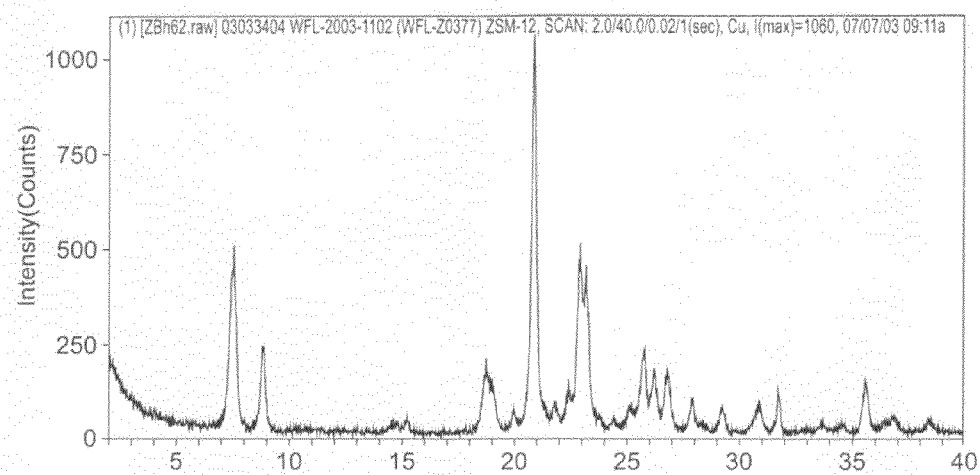
FIG. 2A is XRD of the as-synthesized material of Example 2.

The mixture was reacted at 320° F. (160° C.) in a 19 liter (five gallon) autoclave with stirring at 150 RPM for 120 hours. The product was filtered, washed with deionized (DI) water and dried at 250° F. (120° C.). The XRD pattern of the as-synthesized material showed the typical pure phase of ZSM-12 topology. As can be seen in FIG. 2A, no peaks corresponding to ZSM-5 or mordenite could be detected.

Figure 2B:
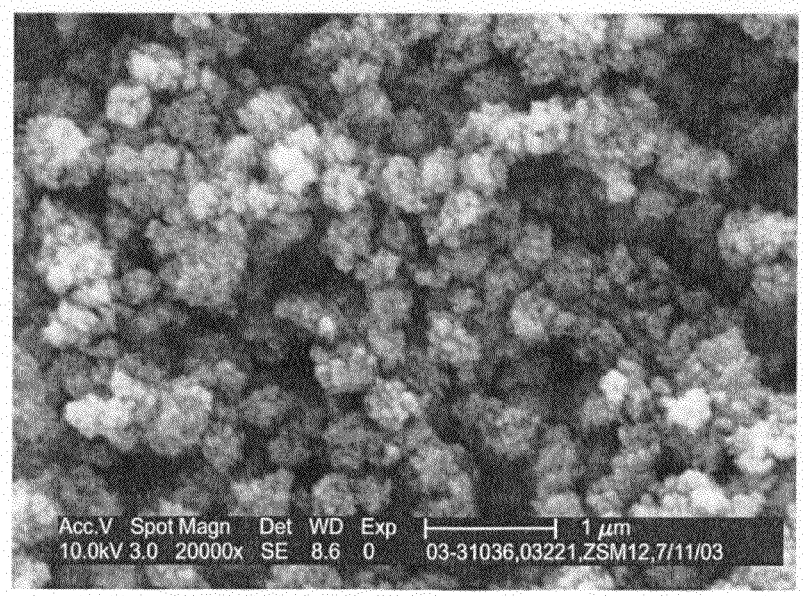
FIG. 2B is SEM of the as-synthesized material of Example 2.

The SEM of the as-synthesized material, as demonstrated in FIG. 2B, showed that the material was composed of agglomerates of small crystals (with an average crystal size of <0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 39.3, an alpha value of 520, and a $D/r^2$ parameter for 1,3,5-trimethyl benzene (mesitylene) at 100° C. of $8,100 \times 10^{-6}$.

EXAMPLE 3

A mixture was prepared from 10,410 g of water, 1,126 g of methyltriethylammonium chloride (MTEACl), 87.5 g of hexamethonium chloride (56% aqueous solution), 1,814 g of Ultrasil silica, 299 g of sodium aluminate (45%) solution, 20 g of ZSM-12 seed crystals, and 310 g of NaOH 50% solution. The mixture had the following molar composition:

$SiO_2/Al_2O_3$~36
$H_2O/SiO_2$~22
$OH^-/SiO_2$~0.21
$Na^+/SiO_2$~0.21
$MTEACl/SiO_2$~0.26
HMDCl/MTEACl~0.026

Figure 3A:
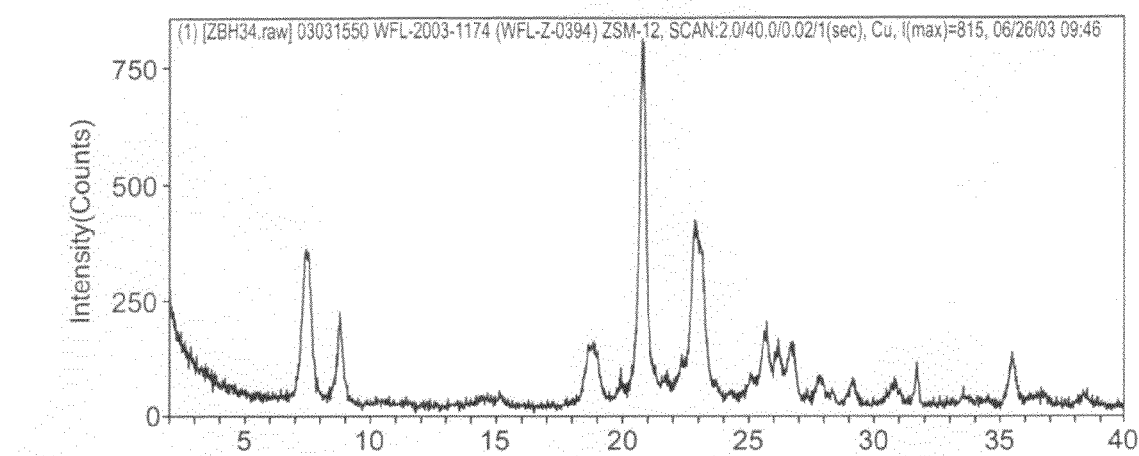
FIG. 3A is XRD of the as-synthesized material of Example 3.
Figure 3B:
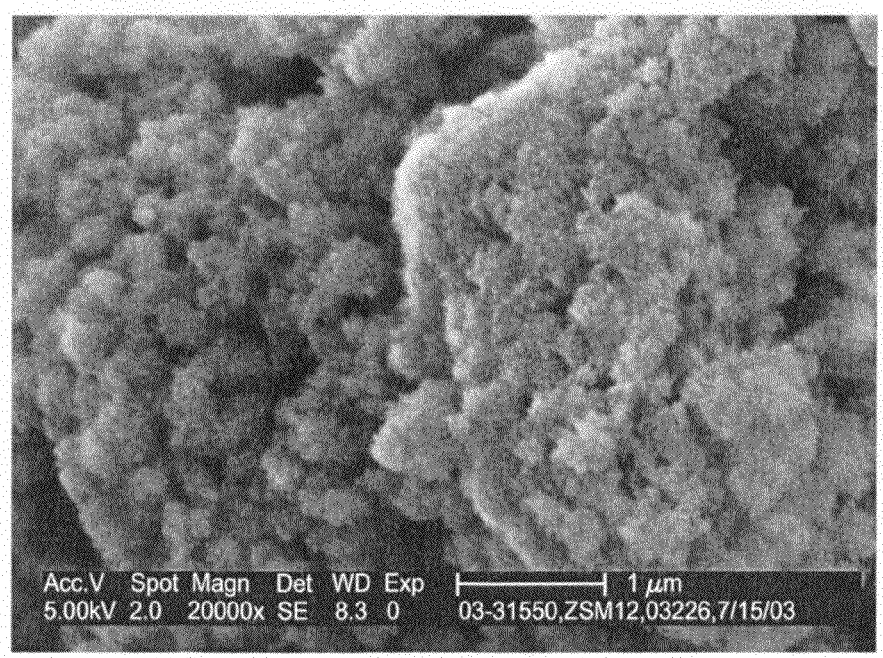
FIG. 3B is SEM of the as-synthesized material of Example 3.

The mixture was reacted at 320° F. (160° C.) in a 19 liter (five gallon) autoclave with stirring at 150 RPM for 144 hours. The product was filtered, washed with deionized (DI) water and dried at 250° F. (120° C.). The XRD pattern of the as-synthesized material showed the typical pure phase of ZSM-12 topology, as shown in FIG. 3A. The XRD showed no sign of the presence of ZSM-5 or mordenite impurities. The SEM of the as-synthesized material, as demonstrated FIG. 3B, showed that the material was composed of agglomerates of small crystals (with an average crystal size of <0.05 microns).

The as-synthesized crystals were converted into the hydrogen form by two ion exchanges with ammonium nitrate solution at room temperature, followed by drying at 250° F. (120° C.) and calcination at 1000° F. (540° C.) for 6 hours. The resulting ZSM-12 crystals had a $SiO_2/Al_2O_3$ molar ratio of 35.5, an alpha value of 470, and a $D/r^2$ parameter for 1,3,5-trimethyl benzene (mesitylene) at 100° C. of $65,000 \times 10^{-6}$.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A porous, crystalline material having the framework structure of ZSM-12 and a composition involving the molar relationship: $X_2O_3:(n)YO_2$, wherein X is a trivalent element, Y is a tetravalent element, and n is less than about 45, wherein the average crystal size of the material is less than about 0.1 micron, which material further contains both an organic monoquaternary ammonium cation, R, and at least one organic diquaternary ammonium cation, R'.

2. The porous, crystalline material of claim 1, wherein n is about 20 to less than about 40.

3. The porous, crystalline material of claim 1, wherein n is about 30 to about 36.

4. The porous, crystalline material of claim 1, wherein X is aluminum and Y is silicon.

5. The porous, crystalline material of claim 1, wherein said material has an alpha value in excess of 400.

6. The porous, crystalline material of claim 1, wherein said material has a Diffusion Parameter for mesitylene of at least about $1000 \times 10^{-6}$ sec$^{-1}$ when measured at a temperature of 100° C. and a mesitylene pressure of 2 torr.

7. A porous, crystalline material having the framework structure of ZSM-12 and a composition in terms of mole ratios of oxides as follows:

$$(a)R_2O:(b)R'_2O:(c)M_{2/n}O:X_2O_3:(d)YO_2$$

wherein R is organic monoquaternary ammonium cation, R' is at least one organic diquaternary ammonium, M is at least one cation having a valence n, X is a trivalent element, Y is a tetravalent element, a ranges from about 0.01 to about 2, b is non-zero and extends up to about 2, c ranges from about 0.01 to about 2, and d ranges from about 20 to about 100.

8. The composition of claim 7, wherein M is sodium, X is aluminum, Y is silicon, and (i) b/a ranges from 0.005 to 0.05, (ii) b/d ranges from 0.001 to 0.02, or (iii) both (i) and (ii).

9. The composition of claim 8, wherein R is $R^1R^2R^3R^4N^+$ wherein each of $R^1$, $R^2$, $R^3$, and $R^4$ are the same or different and selected from the group consisting of $C_1$ to $C_4$ alkyls, R' is $R^5R^6R^7N^+(CH_2)_mN^+R^8R^9R^{10}$ wherein each of $R^5$, $R^6$, $R^7$, $R^8$, $R^9$, and $R^{10}$ are the same or different and are selected from the group consisting of $C_1$ to $C_4$ alkyls.

10. The composition of claim 9, wherein R is methyltriethylammonium and R' is polymethylene bis-trimethylammonium.

11. The composition of claim 10, wherein R' is hexamethonium.

12. A process for synthesizing the porous, crystalline material of claim 1, comprising:
(a) preparing a mixture capable of forming said material, said mixture comprising sources of alkali or alkaline earth metal (M), an oxide of trivalent element (X), an oxide of tetravalent element (Y), hydroxyl ($OH^-$) ions, water, and an organic monoquaternary ammonium cation directing agent (R) and an organic diquaternary ammonium agent (R'), wherein said mixture has a composition, in terms of mole ratios, within the following ranges:

$YO_2/X_2O_3$=less than 50
$H_2O/YO_2$=10 to 100
$OH^-/YO_2$=0.1 to 0.6
$M/YO_2$=0.1 to 0.6
$R/YO_2$=0.1 to 0.6
R'/R=0.01 to 0.10

(b) maintaining said mixture under sufficient conditions until crystals of said material are formed; and (c) recovering said crystalline material from step (b).

13. The process of claim 12, wherein $R=R^1R^2R^3R^4N^+$ wherein each of $R^1$, $R^2$, $R^3$, and $R^4$ are the same or different and selected from the group consisting of $C_1$ to $C_4$ alkyls, R' is $R^5R^6R^7N^+(CH_2)_mN^+R^8R^9R^{10}$ wherein each of $R^5$, $R^6$, $R^7$, $R^8$, $R^9$, and $R^{10}$ are the same or different and selected from the group consisting of $C_1$ to $C_4$ alkyls, and said reaction mixture has a composition in terms of mole ratios within the following ranges:

$YO_2/X_2O_3$=30 to 40
$H_2O/YO_2$=15 to 40
$OH^-/YO_2$=0.15 to 0.4
$M/YO_2$=0.15 to 0.4
$R/YO_2$=0.15 to 0.4
$R'/R$=0.02 to 0.03.

14. The process of claim 13, wherein R is methyltriethylammonium and R' is polymethylene bis-trimethylammonium.

15. The process of claim 14, wherein R' is hexamethonium.

16. The process of claim 12, wherein said conditions include a temperature of 170° C. or less.

17. The process of claim 12, wherein said conditions include a temperature of 140° C. to 160° C.

* * * * *